(12) United States Patent
Chernyshov et al.

(10) Patent No.: US 7,604,870 B2
(45) Date of Patent: Oct. 20, 2009

(54) BIOCOMPATIBLE POROUS TI-NI MATERIAL

(75) Inventors: Alexandr Chernyshov, Sept-Iles (CA); Sylvain Allard, Ste-Julie (CA)

(73) Assignee: Nitinol Devices and Components, Inc., Fremont, CA (US)

( * ) Notice: Subject to any disclaimer, the term of this patent is extended or adjusted under 35 U.S.C. 154(b) by 558 days.

(21) Appl. No.: 10/565,349

(22) PCT Filed: Aug. 8, 2003

(86) PCT No.: PCT/CA03/01213

§ 371 (c)(1), (2), (4) Date: Jan. 20, 2006

(87) PCT Pub. No.: WO2005/014072

PCT Pub. Date: Feb. 17, 2005

(65) Prior Publication Data

US 2006/0228536 A1 Oct. 12, 2006

(51) Int. Cl.
- A61L 27/06 (2006.01)
- A61L 27/56 (2006.01)
- B32B 5/18 (2006.01)

(52) U.S. Cl. ................................ 428/613; 623/23.55

(58) Field of Classification Search .................. None
See application file for complete search history.

(56) References Cited

U.S. PATENT DOCUMENTS

| | | | |
|---|---|---|---|
| 4,732,566 A | 3/1988 | Martucci | |
| 4,948,761 A | 8/1990 | Hida | |
| 4,957,885 A | 9/1990 | Hida | |
| 5,986,169 A | 11/1999 | Gjunter | |
| 6,533,905 B2 | 3/2003 | Johnson et al. | |
| 6,913,622 B2 * | 7/2005 | Gjunter | 623/17.16 |
| 7,192,496 B2 * | 3/2007 | Wojcik | 148/675 |
| 2002/0062154 A1 | 5/2002 | Ayers | |
| 2004/0187980 A1 * | 9/2004 | Jung et al. | 148/563 |
| 2004/0216816 A1 * | 11/2004 | Wojcik | 148/675 |
| 2006/0162493 A1 * | 7/2006 | Yuan et al. | 75/245 |
| 2008/0020229 A1 * | 1/2008 | Taya et al. | 428/613 |

FOREIGN PATENT DOCUMENTS

WO    WO 01/13969    3/2001

OTHER PUBLICATIONS

Li B-Y et al., "Electric Resistance Phenomena in Porous TiNi Shape-Memory Alloys Produced by SHS" Scripta Materialia, Elsevier, New York, NY, U.S., vol. 44, No. 5, Mar. 26, 2001, pp. 823-827.

(Continued)

*Primary Examiner*—John J Zimmerman
(74) *Attorney, Agent, or Firm*—Shay Glenn LLP

(57) ABSTRACT

This invention relates to a porous nickelide of titanium (TiNi) material also comprising oxygen, that is biomechanically and biochemically compatible and is intended primarily for use in the biomedical fields for implantation and interfacing with living tissues. The material has a porous structure defined by morphological, mechanical and surface properties to conform well to adjacent bone to which the TiNi material is designed to bind. The material is further distinguished by a complete lack of nickel enriched secondary phases. These phases may leach nickel into the body which could result in complications associated with nickel toxicity. The mechanical properties and surface characteristics achieved confirm the biofunctionality of the invention.

10 Claims, 5 Drawing Sheets

OTHER PUBLICATIONS

John J. Moore et al., "Combustion Synthesis of Advanced Materials: Part I. Reaction Parameters" Progress in Material Science, vol. 39 (1995), pp. 243-273.

Zuhair A. Munir et al., "Self-Propagating Exothermic Reactions: The Synthesis of High-Temperature Materials by Combustion", Materials Science Reports 3 (1989, pp. 277-365.

J. B. Holt et al., "Self-heating Synthesis of Materials", Annual Review Material Science, 1991, 21:305-334.

Anja Serneels, "Shape Memory Alloy Characterisation and Optimisation", AMT @ Medical Technologies, Daelemveld 1113, 3540 Herk-de-Stad, Belgium.

* cited by examiner

BIOCOMPATIBLE POROUS TI-NI MATERIAL

TECHNICAL FIELD

This invention relates to a porous nickelide of titanium (TiNi) material for use primarily in biomedical fields of implantation to interface with living tissues. The invention has morphological characteristics and mechanical properties that conform well with adjacent bone.

BACKGROUND OF THE INVENTION

Bone is a major component of the human musculoskeletal system. There are two primary types of bone: trabecular bone and cortical bone.

Trabecular or cancellous bone is an interior meshwork of trabeculae (thin struts). Trabecular bone has an elastic modulus in the order of 1 GPa, and a porosity range from 30% to 90%.

Cortical bone is the dense outer shell of bone, which is also known as compact bone. Its porosity ranges from 5% to 30% while with an elastic modulus is about 18 Gpa.

Bone fractures occur when the bone is loaded to failure. Compression fractures are most common in trabecular bone. Bending and torsional fractures are most common in cortical bone. The implantation of a metal or ceramic prosthesis into fractured or diseased regions, subjects the bone to complex stress states. Loosening and subsidence due to failure of the "implant-bone" interface is an important determining factor for the success of a medical treatment. As such, matching of the mechanical properties of the prosthesis to that of the bone is required.

The use of porous surfaces for biological attachment of the implant through ingrowth of the bone greatly improves the fixation of the implanted prosthesis to the bone. However, with the considerable surface area of the porous TiNi material, in contact with body fluids, nickel ion release, from Ni-enriched precipitates present, into these fluids becomes a concern [Assad M., Chernyshov A., et al. *J. Biomed+. Mater.* V.64B, 2, 2003, pp. 121-129], due primarily to the relative toxicity of nickel and nickel salts.

SUMMARY OF THE INVENTION

It is the object of the present invention to provide a porous TiNi material with improved biomechanical and biochemical compatibility with bone while preserving the required porosity and maximizing the fraction of the pores in the range between 50 and 500 μm to allow more efficient bone integration.

It is a further object of the present invention to eliminate nickel enriched secondary phases from the porous TiNi material.

In accordance with one embodiment of the invention there is provided a porous biomechanically and biochemically compatible nickelide of titanium (TiNi) material comprising: a matrix of TiNi comprising interconnected struts, each strut having an outer surface and an internal zone, the matrix having an atomic ratio of Ni:Ti varying from 0.96:1 to 1.13:1 and including a maximum concentration of 10 atomic % of oxygen with the balance being Ni and Ti wherein the Ni concentration is limited to a maximum 53 atomic %; composite precipitates interspersed within the matrix; and a multiplicity of interconnected pores defined by the matrix, wherein the pores have a pore size distribution given as follows;

| Pore Size (μm) | Percentage |
| --- | --- |
| <50 μm | <5% |
| 50 to 500 μm | >75% |
| >500 μm | balance | wherein the material has an open porosity varying from 35 to 80% and the matrix having mechanical properties suitable for surgical implantation, and wherein the matrix is devoid of Ni-enriched secondary phases.

DETAILED DESCRIPTION OF THE PREFERRED EMBODIMENT

Figure 1:
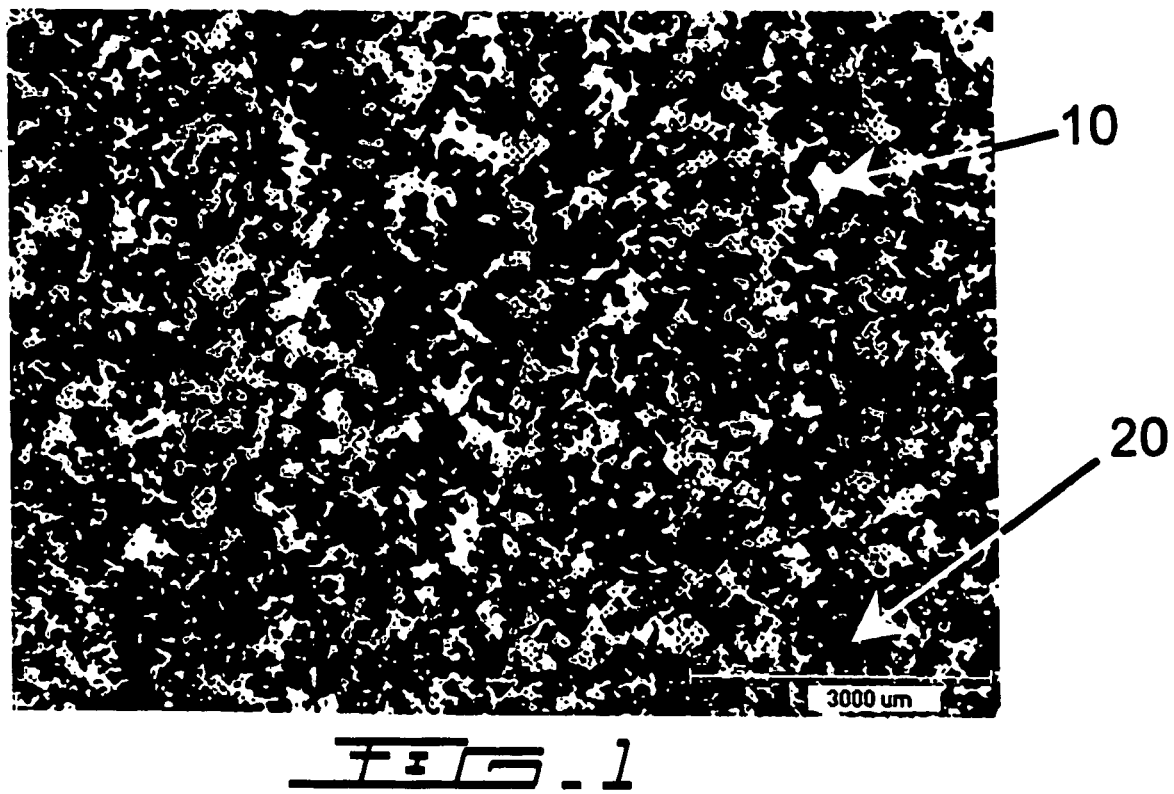
FIG. 1—Macrostructure of the porous TiNi material in the transverse direction (Sample A)

The current invention relates to a novel biocompatible porous TiNi material with defined biochemical and biomechanical characteristics that conform to produce an interface with adjacent bone upon implantation.

Various objects can be produced in accordance with the invention. One especially preferred group of articles is suitable for medical implantation. The porous TiNi implants of this invention have properties similar to those of bone, and produce the appropriate properties for bio-functionality and allow the material to interface with living tissues.

The properties of the implant include:
- maximizing the percentage of pores in a range between 50 and 500 μm;
- a porosity matching the properties of the surrounding bone;
- mechanical properties capable of withstanding the complex loading conditions that exist in a human body; and importantly
- surface properties that minimize the release of nickel ions by reducing the amount of Ni-enriched secondary phases to virtually zero.

The following guidelines for the design of a porous TiNi material having the appropriate biomechanical compatibility have been formulated from the analysis of mechanical properties of bone tissue under various physiological conditions.

Under moderate physiological conditions (small strains):
- The implanted material should match the modulus of elasticity of the bone to prevent a large stress shielding at the "implant-bone" interface;
- The actual yield strain/stress values of the implanted material under tension and compression must be higher than that for the trabecular bone to consider the required performance under cyclic loading.

Under higher or extreme conditions (high strains):
  The material of the implant should have a higher ultimate strength than surrounding bone.
  The material should demonstrate good viscoelastic and damping properties in order to minimize the energy that has to be absorbed by the bone. This requires the maximization of the energy absorption characteristics for the implanted material.

Some properties of trabecular bone at small strains are presented in Table 1, where E is the elastic modulus, $\sigma_y$ is the yield strength and $\epsilon_y$ is the maximum elastic deformation.

TABLE 1

Yield properties ± Standard deviation of trabecular bone at different anatomic sites.

| Anatomic site | Loading mode | 0.02-0.24% strain | | |
|---|---|---|---|---|
| | | E, Gpa | $\sigma_y$, MPa | $\epsilon_y$, % |
| Vertebra | Compression | 0.32 ± 0.13 | 2.11 ± 0.97 | 0.85 ± 0.06 |
| | Tension | 0.32 ± 0.13 | 1.83 ± 0.68 | 0.78 ± 0.05 |
| Proximal Tibia | Compression | 1.06 ± 0.60 | 6.25 ± 3.45 | 0.80 ± 0.05 |
| | Tension | 0.87 ± 0.65 | 4.38 ± 3.19 | 0.72 ± 0.04 |
| Trochanter | Compression | 0.56 ± 0.28 | 3.37 ± 1.91 | 0.78 ± 0.05 |
| | Tension | 0.52 ± 0.29 | 2.58 ± 1.30 | 0.71 ± 0.06 |
| Bovine tibial | Compression | 0.7-2.3 | 20.64 ± 0.59 | 1.09 ± 0.12 |
| | Tension | 1.1-1.5 | 14.36 ± 0.33 | 0.78 ± 0.04 |

[References for Table 1: Morgan E. F., Yeh O. C., et al. Nonlinear behavior of trabecular bone at small strains. *J. Biomech. Eng.*, V.123, February 2001, pp. 1-9; and Keaveny, T. M., Wachtel, E. F., Ford, C. M., and Hayes, W. C., "Differences between the tensile and compressive strengths of bovine tibial trabecular bone depend on modulus," *J. Biomech.*, Vol. 27, 1994, pp. 1137-1146]

The mechanical properties of the trabecular and cortical bones under extreme conditions and high strains are presented in the Table 2:

TABLE 2

Mechanical properties of the bone for prediction of the fracture.

| Bone type (Strain to Failure) | Load type | Elastic Modulus, GPa | Ultimate Strength, MPa |
|---|---|---|---|
| Cortical (2%) | Compression | 15.1-19.7 | 156-212 |
| | Tension | 11.4-19.1 | 107-146 |
| Trabecular (<75%) | Compression | 0.1-3 | 1.5-50 |
| | Tension | 0.2-5 | 3-20 |

[References for Table 2: Neibur G. L. "A computational investigation of multiaxial failure in trabecular bone", *Ph.D. Thesis*. The University of California, Berkeley, USA; Guo E. Mechanical Properties of cortical bone and cancellous bone tissue. In: Cowin S.C., Eds. *Bone Mechanics handbook*. Boca Raton, Fla.: CRC Press LLC, 2001; Moroi H. H., Okimoto K., Moroi R., and Terada Y. *Int. J. Prosthodont*, 6:, 1993, pp. 564-572; Frankel V. H., Nordin M. "Basic Biomechanics of the Skeletal System", Philadelphia, Lea & Febiger, 1980].

Several important properties define what makes a porous TiNi implant biomechanically compatible with natural bone. At normal functional strain levels these properties are: a) the modulus of elasticity, b) the maximal elastic deformation and c) the yield strength. Under conditions of considerable non-elastic deformation up to and including the failure breakpoint, the properties are d) the ultimate strength, e) the maximum strain to failure, f) the viscoelasticity and g) the energy that can be absorbed before fracture.

The modulus of elasticity, defines the stress shielding effect at the "bone-implant" interface, where stress shielding induces the reaction of the organism to compensate for the difference in elastic properties of the adjacent bone and the implant with the formation of fibrous tissue at the "bone-implant" interface. The maximal elastic deformation indicates the probable performance of the material under actual in-vivo conditions and cycling loading. The yield strength may have direct bearing on energy dissipation mechanisms. The ultimate strength represents the maximum load that material can sustain before it breaks. The maximum strain to failure is self-explanatory. Viscoelasticity refers to creep, strain, stress relaxation or a combination thereof. The energy absorbed before fracture is obtained from the total area below the "stress-strain" curve (30, in FIG. 4) and thus depends on both the ultimate stress and the ultimate strain. Although not previously mentioned above, higher porosity is desirable because it maximizes energy absorption due to scattering of waves.

This invention relates to a porous nickelide of titanium (TiNi) material that is biomechanically and biochemically compatible and is intended primarily for use in the biomedical fields for implantation as a surgical implant. The material can be used anywhere the attachment to bone is required, and is particularly useful in cervical implants, lumbar fusion devices, vertebral replacement devices, artificial discs, and acetabular cup replacements (in the hip).

A porous TiNi product that has a stress plateau under compression test conditions without oblique fracture is a porous TiNi material having a maximized energy absorbed before failure and consequently improved damping properties.

Table 3 presents an optimal set of mechanical properties under compressive load, for a porous TiNi material sought after in biomedical applications, making the material biomechanically compatible with the bone tissue to which it is connected:

TABLE 3

Mechanical properties of a preferred embodiment of porous TiNi material.

| | Mechanical characteristic | Selection criteria | Optimal values |
|---|---|---|---|
| a) | Elastic Modulus, GPa | elastic modulus of the bone | 0.1-3.0 |
| b) | Max. Elastic Deformation, % | more than yield strain of the bone | >2 |
| c) | Yield strength, MPa | more than yield stress of the bone | 1.5-50 |
| d) | Ultimate Strength, MPa | ultimate strength of the bone | 50-250 |
| e) | Maximum Strain to failure, % | maximum value for the bone | up to 75 |
| f) | Viscoelasticity | stress plateau at strain-stress curve | — |
| g) | Energy absorbed before failure | no oblique fracture under compression | maximized |

Biomechanical compatibility is defined as the absence of stress shielding at the "implant-bone" interface.

In the present invention, the control of the properties of the porous TiNi materials are obtained through the distribution or allocation of oxygen content throughout the matrix of the TiNi. This can be achieved by any number of means which include air scavenging, purging the reactor mould with inert gas and raw material selection.

The process for the production of the TiNi material may be a Self-propagating High temperature Synthesis (SHS) reaction or other process such as sintering. Where in SHS the propagation is produced in accordance with the procedures understood by a skilled practitioner. Which includes a progressive combustion that uses the exothermic heat emitted during the reaction of the nickel and titanium.

Small deviations from the required stoichiometric ratio in the raw material mixture prior to the SHS reaction may significantly increase secondary-phase formation and adversely affect the mechanical characteristics of the TiNi material including shape-memory and superelastic properties [Lopez H. F., Salinas A., Calderon H., *Metallurgical and Materials Transactions* A. V.32A, March 2001, pp. 717-729]. The appearance of the Ni-enriched secondary phases may increase the release of the Ni ions. The recoverable strain is strongly influenced by Ni content, thermo-mechanical treatment and the transformation sequence exhibited by the alloy during thermal cycling. Several important features help to define the quality of the product: the Ti and Ni raw materials must be premixed into a highly homogeneous mixture; high reproducibility of the properties; reliable control over the technological parameters in the course of production. This particularly applies to a biomedical implant that is designed to match the properties of adjacent bone to achieve the required biofunctionality and to promote an efficient healing response.

The current invention is a biocompatible porous TiNi material having a combination of optimal properties and characteristics that match those of adjacent bone tissue and that it is devoid of Ni-enriched secondary phases. In this specification "devoid" is understood as a concentration level that cannot be detected by SEM (Scanning Electron Microscopy) or TEM (Transmission Electron Microscopy) analyses. The TiNi material thus devoid of Ni-enriched secondary phases, reduces the likelihood to virtually zero, that the secondary phases may leach nickel into the body, where such leaching may result in complications associated with nickel toxicity. The SEM equipment used was JEOL JSM-840 coupled to an ultra thin window (UTW) energy dispersive X-ray spectrometer (EDS). The used TEM was the Philips CM-30 300 kV.

The invention is demonstrated with reference to the following examples:

EXAMPLE # 1

Sample A

Sample A represents a porous TiNi material obtained by means of SHS technique. The combination of its morphological and mechanical characteristics is in the optimal range proposed in Table 3.

Figure 2:
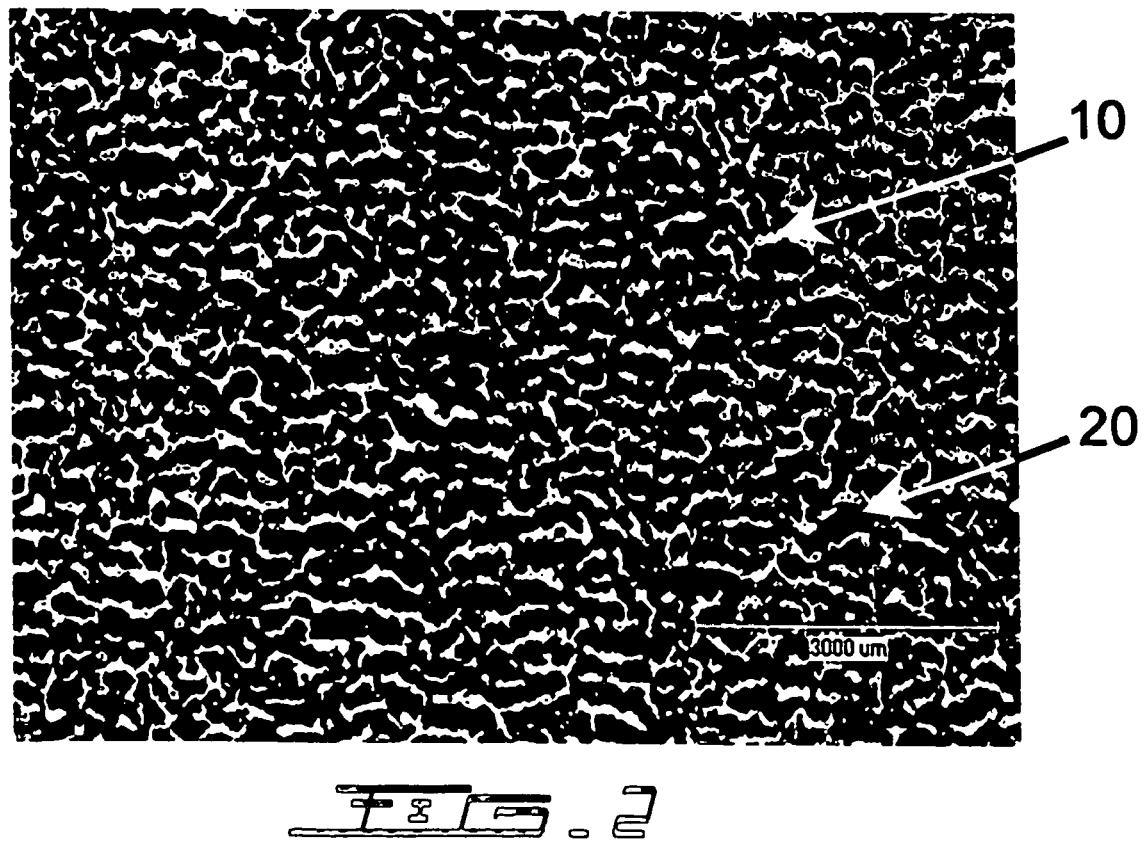
FIG. 2—Macrostructure of the porous TiNi material in the longitudinal direction (Sample A)
Figure 3:
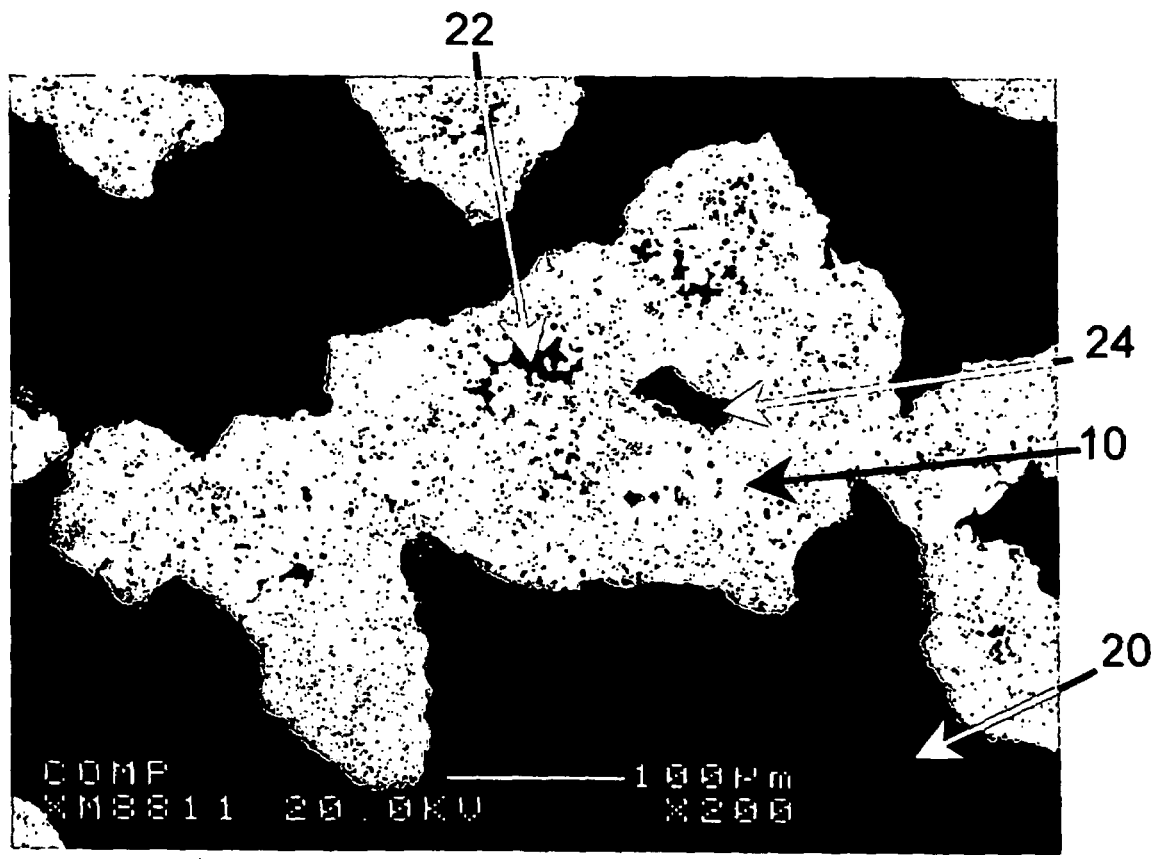
FIG. 3—Microstructure of the porous TiNi material (Sample A)

Sample A has a porosity in a range of 63±1.2%. FIGS. 1 and 2 present the two dimensional (2D) macrostructure of the porous synthesized material in the transverse and longitudinal directions respectively. The porous material includes a TiNi matrix (a framework of interconnected struts), the lighter zones (10) and porosity (20) the darker zones. The defined porosity includes both "open" and "closed" pores. FIG. 3 shows the "Open" pores (20) which are defined as interconnected pores that form a continuous network. The percentage of the "open" pores reflects the volume that most probably will promote bone ingrowth. The percentage of "closed" pores (24) is related to the volume of the pores that have low probability of promoting any bone ingrowth within the product because they are too small or probably not interconnected. The data regarding pore size distribution is presented in the Table 4.

TABLE 4

Pore Parameters, Sample A.

| Pore Distribution | | Statistics On open pore dimensions, μm | |
|---|---|---|---|
| Size, μm | Percentage, % | | |
| | | Minimum | 4-27 |
| <50 | 1-2 | Maximum | 689-1013 |
| 50-500 | 93-97 | Mean | 192-225 |
| >500 | 2-5 | Std. Dev. | 91-119 |

The characterisation of the solid objects (struts) of the TiNi matrix of the Sample A is presented in Table 5.

TABLE 5

Solid Objects of the TiNi Matrix, Sample A

| Statistics | AREA, (A) μm$^2$ | CONVEX PERIMETER, (CP) μm | COMPACTNESS ($4\pi A/CP^2$) |
|---|---|---|---|
| Minimum: | 6.8-7.0 | 8.0-8.2 | 0.02-0.14 |
| Maximum: | 547876-1071025 | 4165-5918 | 1 |
| Mean: | 6946-13151 | 173-309 | 0.71-0.79 |
| Std Dev.: | 36774-52875 | 386-520 | 0.19-0.24 |

The characteristics of the struts (or solid objects) are defined as follows:

The statistically determined area (A) of the struts is proportional to the ultimate strength and rigidity of the porous material with all other factors being equal;

The Convex Perimeter (CP) of the struts is an indirect parameter of the surface area in contact with adjacent tissues;

The Compactness ($4\pi A/(CP)^2$) of each strut within the TiNi matrix provides indirect information concerning processing conditions. Rounder struts may indicate greater liquid phase involvement during the SHS reaction. Completely round solid objects have a compactness value of 1.

The microstructure of the TiNi struts is presented on FIG. 3. At a (200×) magnification the details of the TiNi matrix (10) can be clearly distinguished. The precipitates (22) are Ti-enriched secondary phases. A smoother matrix surfaces and a lower quantity of the visible Ti-enriched secondary phases leads to better homogeneity of the sample.

The TiNi matrix of Sample A has a local content of Ti-enriched secondary phases in the range of 6-11%. The Ti-enriched precipitates have a mean diameter of 2-4 μm, with the maximum outer diameter from 27-96 μm (Table 6).

TABLE 6

Precipitates characteristics Sample A.

| Ti-enriched precipitates, distribution | | Statistics On dimensions of Ti-rich precipitates, μm | |
|---|---|---|---|
| Size, μm | Percentage, % | | |
| | | Minimum | 0.6-1 |
| | | Maximum | 27-96 |
| <10 | 95 | Mean | 2-4 |
| >10 | 5 | Std. Dev. | 2-4 |

In FIG. 3, we see the presence of the Ti-enriched phases (22) in form of "splashes". This shape of Ti-enriched secondary phases is not desirable because it may lead to nucleation of cracks along the Ti-enriched "splash extensions". However an oxygen content in Ti-enriched phases in the range of 2.3-3.4 at. % (Table 7) leads to the preferred values of mechanical properties found in Table 3.

TABLE 7

Chemical composition of porous TiNi material at different locations.

| | Sample A | | | | | |
|---|---|---|---|---|---|---|
| | Internal Zone of the Struts | | | Outer Surface of the Struts | | |
| Re: | Ti, at. % | Ni, at. % | O, at. % | Ti, at. % | Ni, at. % | O, at. % |
| TiNi Matrix | 49.4 | 49.0-49.4 | 1.2-1.7 | 45.9-47.7 | 47.2-49.5 | 3.2-6.9 |
| Ti-enriched phases | 64.4-64.8 | 32.2-32.9 | 2.3-3.4 | 51.7-54.2 | 28.0-30.2 | 17.8-18.1 |
| Ni-enriched phases** | — | — | — | — | — | — |

**Note:
The Ni-enriched phases were detected at the outer periphery of the porous bar to a depth of 1625 μm With reference to the data presented in the Table 7, the maximum oxygen content in the matrix has been found at the outer surface of the struts. The oxygen value was recorded at 6.9 at. %, which corresponds to 2.16 wt. % (The oxygen content was obtained by an Electronic Probe Micro Analysis, EPMA, technique).

Figure 7:
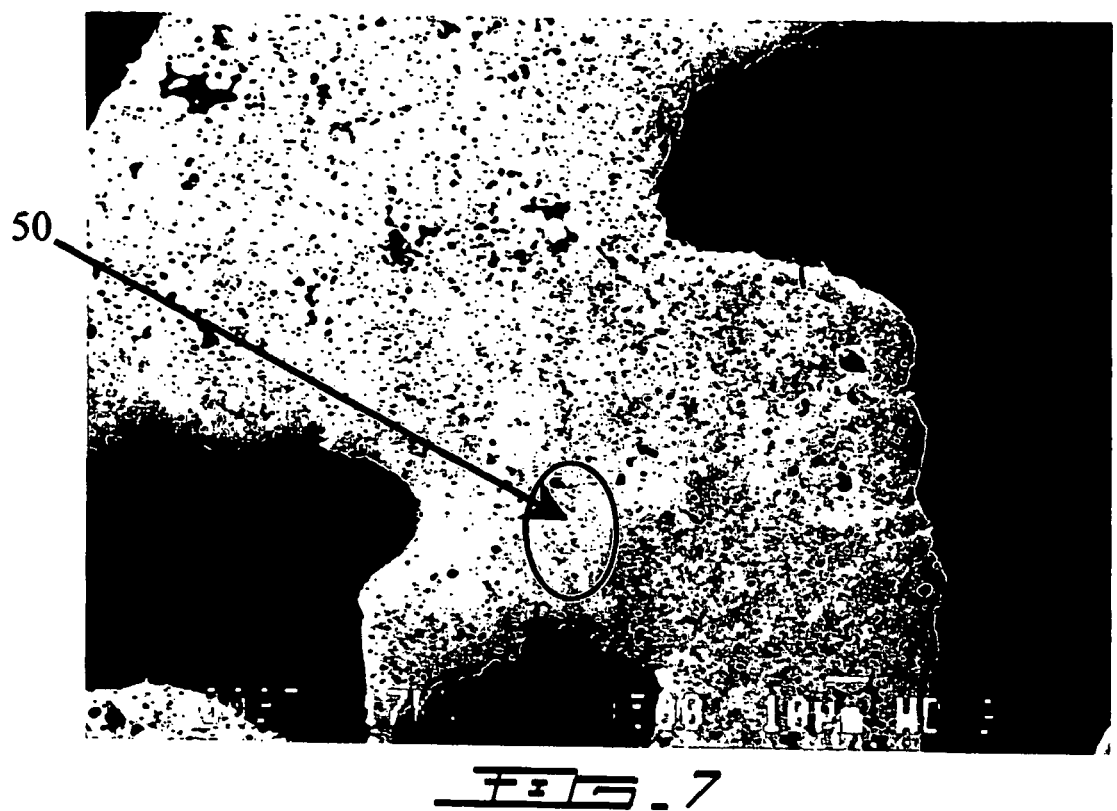
FIG. 7—Back Scattered electron SEM micrograph of Ni-enriched secondary phases and Ti-enriched secondary phases in the periphery of Sample A (500×)
Figure 8:
FIG. 8—Back Scattered electron SEM micrograph of Ni-enriched secondary phases and Ti-enriched secondary phases in the periphery of Sample A (3000×).

Using chemical etching, the Ni-enriched precipitates (52) were detected mainly at the periphery of the porous TiNi product (FIG. 8). A Ni-enriched zone (50) can be clearly seen in the FIG. 7. We see that the composite precipitates within the matrix comprise Ni-enriched secondary phases that can be visually distinguished easily from the Ti-enriched secondary phases (22). The Ni-enriched secondary phases are also found throughout the matrix although to a far lesser extent. The preponderance of Ni-enriched secondary phases at the boundary of the TiNi product is due to heat losses and segregation of initial components at the interface surrounding the mould. The depth of Ni-enriched secondary phases may characterise the extent of non-equilibrium solidification conditions that induce their formation. The maximum depth of Ni-enriched secondary phases sets the depth of machining required to remove these unwanted formations. In case of the Sample A, the Ni-enriched secondary phases were detected at the periphery of the cylindrical bar at a penetration distance of not more than 1625 μm. To ensure the absence of the vast majority of the Ni-enriched secondary phases in the final product, at least 2 mm of the porous TiNi was machined off its periphery. Sample A still contained a minor amount of Ni-enriched secondary phases in the matrix after machining that could not be quantified with accuracy.

Using the ASTM E8-96a method, the mechanical properties of five replicates of porous TiNi samples of the invention and prior art samples[Chernyshov A., Leroux M., et. al. Influence of porous TiNi morphology on mechanical properties. Proceedings "Advanced Materials for Biomedical Applications", MetSoc'2002, 41-th Annual Conference, Aug. 11-14, 2002, Montreal, pp. 109-119] were compared. Tables 8-10 show the substantial improvement of the compression, tensile and fatigue test characteristics over material of the prior art.

TABLE 8

Compression test data.

| Property | Sample A | Prior art [2002] |
|---|---|---|
| Elastic Modulus, GPa | 0.5-0.76 | 0.8-2.1 |
| Yield Strength 0.2%, MPa | 39.0-46.0 | 10.6-33.9 |
| Maximal Elastic Deformation, % | 6.1-8.0 | 1.8-5.8 |
| Ultimate Strength, Mpa | 201-224 | 34-85 |
| Strain to Failure, % | 49.0-54.1 | 11.0-36.9 |

TABLE 9

Tensile test data.

| Property | Sample A | Prior art [2002] |
|---|---|---|
| Elastic Modulus, GPa | 0.27-1.05 | 0.68-0.99 |
| Yield Strength 0.2%, MPa | 6.7-11.3 | 9.4-14.4 |
| Maximal Elastic Deformation, % | 1.0-3.9 | 1.5-2.7 |
| Ultimate Strength, Mpa | 12.9-22.3 | 13.8-16.6 |
| Strain to Failure, % | 5.2-9.1 | 2.4-3.7 |

TABLE 10

Fatigue test data.

| | Fatigue life @ 5 Hz, cycles | |
|---|---|---|
| Load, N (max) | Sample A | U.S. Pat. No. 5,986,169 |
| 2500 | 5,000,000 | 5,000,000 |
| 3000 | 5,000,000 | failed at 688,032 |
| 3500 | 5,000,000 | failed |

Figure 4:
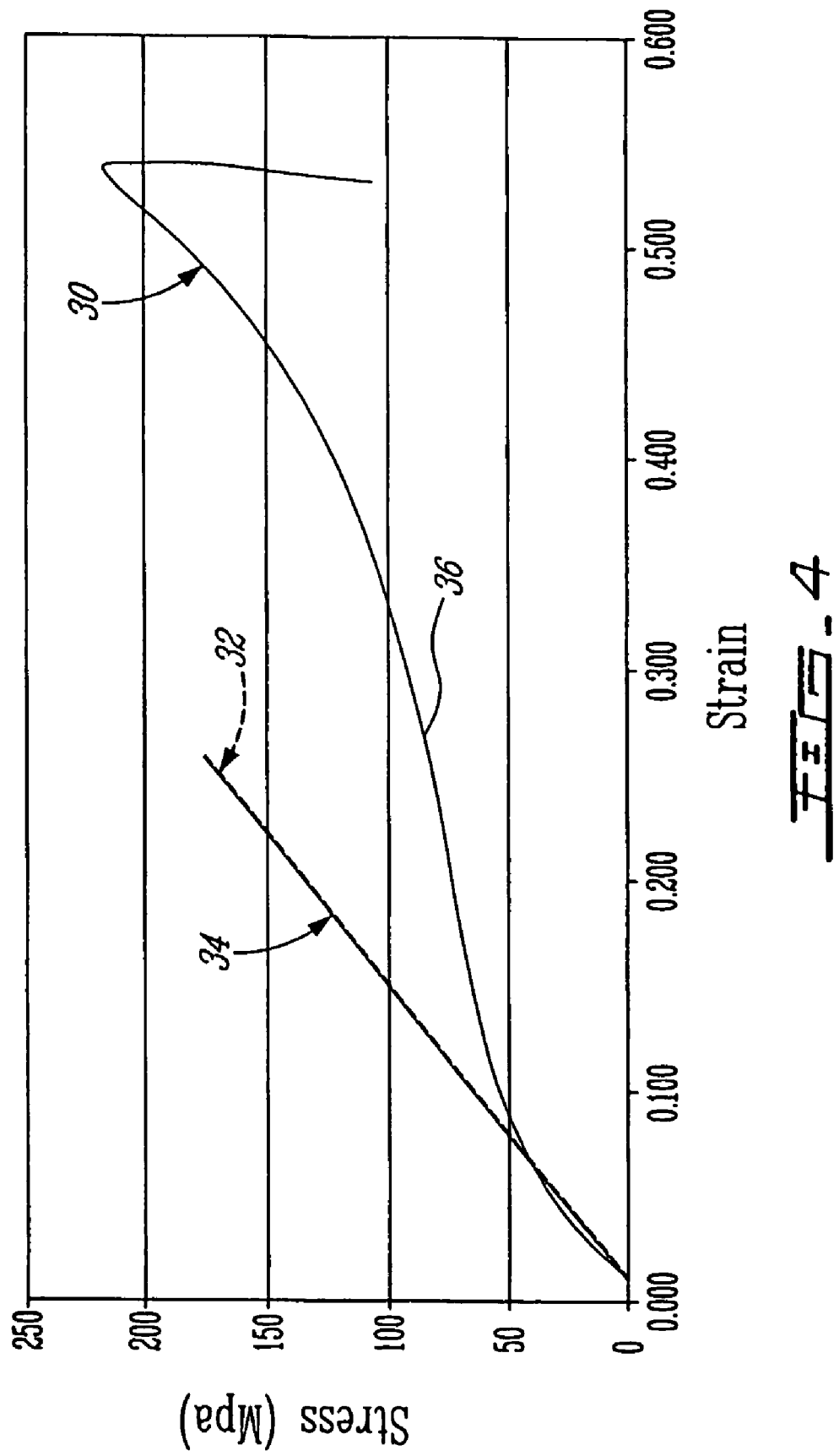
FIG. 4—Typical "Stress-strain" curve under compression test conditions, (Sample A)

The typical "stress-strain" curve (30) for the sample A under compression test conditions is shown on FIG. 4. FIG. 4 further represents the 0.2% strain curve (32) represented by the dashed line; the linear correction curve (34, the solid line) and shows the point of inflection or stress plateau (36).

Sample A once again shows a substantial difference from the behaviour of the prior art material [Chernyshov A., Leroux M., et. al. ibid.]. The prior art material exhibited the oblique fracture under compression test conditions. While with sample A there was no oblique fracture even at more than 49% strain and a stress plateau (36) was recorded. The A samples were characterised with higher ultimate strength than that of cortical bone, confirming a maximized energy absorption before fracture and improved damping properties. These morphological and mechanical characteristics allows us to conclude that Sample A has improved biofunctionality over that previously observed with porous TiNi materials.

EXAMPLE # 2

Sample B

Figure 5:
FIG. 5—Microstructure of the porous TiNi material (Sample B)

Sample B represents a porous TiNi material with morphological and mechanical characteristics similar to those observed for the Sample A. In FIG. 5, we see that the Ti-enriched secondary phases (22) are smaller and a similar chemical components distribution (Table 11).

TABLE 11

Chemical composition of porous TiNi material at different locations (Sample B).

| | Sample B | | | | | |
|---|---|---|---|---|---|---|
| | Internal Zone of the Struts | | | Outer Surface of the Struts | | |
| Re: | Ti, at. % | Ni, at. % | O, at. % | Ti, at. % | Ni, at. % | O, at. % |
| TiNi Matrix | 48.3-49.0 | 49.1-50.0 | 1.7-1.9 | 45.8-51.7 | 44.6-50.7 | 0.4-9.4 |
| Ti-enriched phases | 56.2-57.5 | 29.1-29.5 | 13.0-14.6 | 51.8-61.8 | 21.7-43.2 | 5.9-25.6 |
| Ni-enriched phases | — | — | — | — | — | — |

Sample B was produced by the same SHS technique used in Sample A but was further annealed under an argon atmosphere. Annealing was conducted at 1000° C. for 60 minutes, and more preferably at 1100° C. fro 45 minutes. Sample B exhibited the complete absence of Ni-enriched secondary phases within the matrix and more homogeneous chemical composition, which is due to the annealing step. The higher oxygen content on the surface of the TiNi struts and a lower Ni content is a desirable outcome. In general the higher oxygen content on a surface improves corrosion resistance (biochemical compatibility) of the TiNi materials.

By lowering the Ni-enriched secondary phases to virtually zero, the likelihood of nickel leaching from the implant approaches zero, while maintaining the biofunctionality of the product. The material is distinguished by a complete lack of nickel enriched phases. These phases may leach nickel into the body which could result in complications associated with nickel toxicity.

EXAMPLE # 3

Sample C

Sample C was produced in the same manner as Sample B but raw Ti powder used had a higher oxygen content. Sample C has a total porosity of 65%-68.0%. The pore parameters of Sample C are presented in the Table 12.

TABLE 12

Pore Parameters, Sample C.

| Pore Distribution | | Statistics on pore | |
|---|---|---|---|
| Size, μm | Percentage, % | | dimensions, μm |
| | | Minimum | 5-29 |
| <50 | 1-2 | Maximum | 915-1752 |
| 50-500 | 78-86 | Mean | 294-369 |
| >500 | 13-20 | Std. Dev. | 145-245 |

The TiNi matrix had a local content of Ti-enriched secondary phases in amount of 14.35%.

Sample C represents a porous TiNi material that meets the optimal set of mechanical characteristics proposed in Table 3. Sample C furthermore has smaller and more rounded Ti-enriched precipitates (44) seen in FIG. 6 and distribution of the chemical components (Table 13).

TABLE 13

Chemical composition of porous TiNi material at different locations.

| | Sample C | | | | | |
|---|---|---|---|---|---|---|
| | Internal Zone of the Struts | | | Outer Surface of the Struts | | |
| Re: | Ti, at. % | Ni, at. % | O, at. % | Ti, at. % | Ni, at. % | O, at. % |
| TiNi Matrix | 46.1-46.3 | 51.5-52.0 | 1.9-2.2 | — | — | — |
| Ti-enriched phases | 55.0-55.6 | 28.0-29.0 | 15.4-16.9 | 46.3-54.2 | 24.5-37.3 | 13.8-23.2 |
| Ni-enriched phases | — | — | — | — | — | — |

Figure 6:
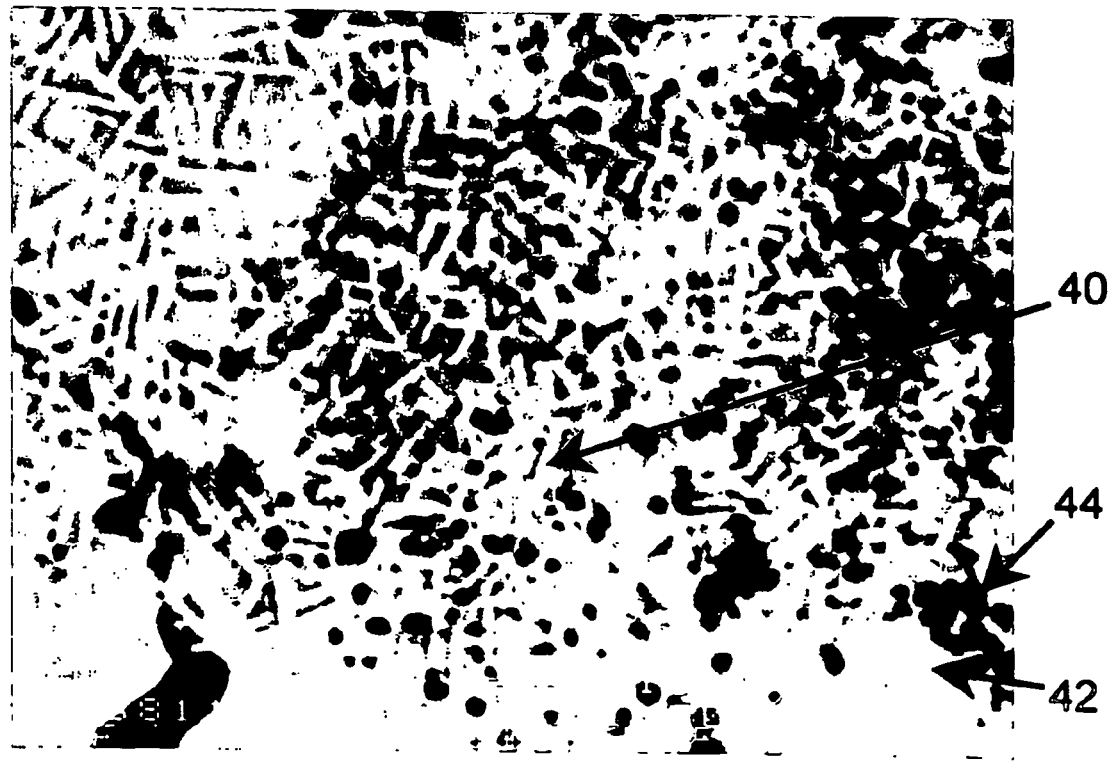
FIG. 6—Microstructure of the porous TiNi material (Sample C)(1500×)

The TiNi matrix of Sample C seen in FIG. 6, displays a martensite matrix with localized areas of austenite needle-like formations (40) between which are found zones of martensitic phases (42).

EXAMPLE # 4

Sample D

To test the impact of the distributed oxygen content on mechanical properties of the porous TiNi material dedicated tests were conducted. A porous TiNi material was produced, with an oxygen content of 4.6 at. % (1.4 Wt. %) evenly distributed in the struts internal zone. The resulting mechanical properties were substantially inferior to the optimal set of values (Table 3), the ultimate strength was lower than 10 MPa. In addition the influence of the surface oxygen content on Ni:Ti ratio was verified and is presented in Table 14.

TABLE 14

Influence of the oxygen content on Ni:Ti ratio.

Chemical composition on the outer surface of the struts

| O, at. % | Ti, at. % | Ni, at. % | Ni:Ti ratio |
|---|---|---|---|
| 3.3 | 47.2 | 49.5 | 1.05:1 |
| 4.6 | 47.7 | 47.6 | 0.99:1 |
| 6.9 | 45.9 | 47.2 | 1.03:1 |
| 9.4 | 60.7 | 29.9 | 0.49:1 |
| 11.2 | 51.2 | 37.5 | 0.73:1 |
| 14.3 | 53.4 | 32.3 | 0.60:1 |
| 20.8 | 51.8 | 27.4 | 0.53:1 |

As seen in Table 14, the maximum content of the oxygen which permits the nickelide of titanium formation is 10 atomic %. At higher oxygen levels on the surface of TiNi struts leads to a substantial redistribution of the Ni:Ti ratio resulting in a presence of Ti-enriched secondary phases. The elevated oxygen content and Ti-enriched secondary phases are desirable on a surface of TiNi strut in view of the required biochemical compatibility and corrosion resistance. It must be noted that Ni:Ti ratios other than 0.96:1 to 1.13:1 lead to substantially diminished mechanical properties for the TiNi intermetallic.

Surprisingly, a maximum oxygen content of 10 atomic. % at the struts outer surface preserves the nickelide of titanium matrix while maintaining an optimal set of mechanical properties of the material.

EXAMPLE # 5

In order to extend the range of the possible shapes of the porous TiNi material, the porous TiNi embodiments described in Examples 1-4 were crushed into powder form. This powder was sieved into a particle size range of about 100-500 micrometers and consequently sintered at temperature lower than melting point of nickelide of titanium. The resulting porous TiNi material had the desirable biochemical, biomechanical and corrosion resistant properties, this indicates wider possible production means for porous TiNi articles.

Changes and modifications may be made by a skilled person in the art, without deviating from the spirit and the scope of the invention. The above examples of the embodiment are for illustration of the invention only and are not intended to limit the scope of the invention.

The invention claimed is:

1. A porous biomechanically and biochemically compatible nickelide of titanium, TiNi material comprising:
   a matrix of TiNi comprising interconnected struts, each strut having an outer surface and an internal zone, the matrix having an atomic ratio of Ni:Ti varying from 0.96:1 to 1.13:1 and including a maximum concentration of 10 atomic % of oxygen with the balance being Ni and Ti wherein the Ni concentration is limited to a maximum 53 atomic %;
   composite precipitates interspersed within the matrix; and
   a multiplicity of interconnected pores defined by the matrix, wherein the pores have a pore size distribution given as follows;

| Pore Size (μm) | Percentage |
|---|---|
| <50 μm | <5% |
| 50 to 500 μm | >75% |
| >500 μm | balance | wherein the material has an open porosity varying from 35 to 80% and the matrix having mechanical properties suitable for surgical implantation, and
   wherein the matrix is devoid of Ni-enriched secondary phases.

2. The material according to claim 1, wherein the matrix has an atomic ratio of Ni:Ti varying from 0.99:1 to 1.04:1 and including a maximum concentration of 2.2 atomic % of oxygen in the internal zone with the balance being Ni and Ti.

3. The material according to claim 1, wherein the composite precipitates comprise Ti-enriched secondary phases comprising oxygen limited to a maximum of 28 atomic % and the balance is Ni and Ti, wherein the atomic ratio of Ni:Ti varies from 0.37:1 to 0.95:1.

4. The material according to claim 3, wherein the Ti-enriched secondary phases comprise oxygen between 2.0 and 17.0 atomic % and the balance is Ni and Ti, wherein the atomic ratio of Ni:Ti varies from 0.49:1 to 0.53:1.

5. The material according to claim 3, wherein the Ti-enriched secondary phases comprise oxygen between 2.3 and 3.4 atomic %.

6. The material according to claim 3, wherein the Ti-enriched secondary phases have a spheroid configuration and an average diameter of 10 μm.

7. The material according to claim 1, wherein the composite precipitates within the matrix are limited to less than 15% by volume.

8. The material according to claim 1, wherein the matrix comprises martensite and austenite.

9. The material according to claim 1, wherein the mechanical properties of the matrix comprise:
   an elastic modulus under compression between 0.2 and 3.0 GPa;
   a maximal elastic deformation more than 2%;
   an ultimate strength between 50 and 250 Mpa;
   strain to failure up to 75%; and
   a yield strength between 1.5 to 50 MPa.

10. The material of claim 3, wherein the Ti-enriched secondary phases comprise oxygen between 13 and 14.6 atomic %.

* * * * *

UNITED STATES PATENT AND TRADEMARK OFFICE
CERTIFICATE OF CORRECTION

PATENT NO. : 7,604,870 B2  Page 1 of 1
APPLICATION NO. : 10/565349
DATED : October 20, 2009
INVENTOR(S) : Chernyshov et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 831 days.

Signed and Sealed this

Fifth Day of October, 2010

David J. Kappos
*Director of the United States Patent and Trademark Office*